US00PP11455P

United States Patent [19]

Layne

[11] Patent Number: Plant 11,455

[45] Date of Patent: Jul. 18, 2000

[54] 'AC HARROW FAIR' PEACH

[75] Inventor: Richard E. C. Layne, Ontario, Canada

[73] Assignee: Agriculture and Agri-Food Canada, Ontario, Canada

[21] Appl. No.: 09/025,757

[22] Filed: Feb. 18, 1998

[51] Int. Cl.[7] ..... A01H 5/00

[52] U.S. Cl. ..... Plt./197

[58] Field of Search ..... Plt./197, 198

[56] References Cited

U.S. PATENT DOCUMENTS

P.P. 8,169 3/1993 Friday ..... Plt./198
P.P. 8,597 2/1994 Viscarra ..... Plt./198

OTHER PUBLICATIONS

Sharon Hill, "Scientist Peachy Keen on New Fruit Varieties", Windsor Star, p. B!, Feb. 5, 1996.

Dr. Bill Shane, "Fresh Market Peach Varieties for Cooler Climates", Compact Fruit Tree vol. 30, pp. 89–91, Feb. 22, 1997.

*Primary Examiner*—Howard J. Locker
*Assistant Examiner*—Wendy A Baker
*Attorney, Agent, or Firm*—Flynn, Thiel, Boutell & Tanis, P.C.

[57] ABSTRACT

A new and distinct variety of peach tree, which has been given the designation 'AC Harrow Fair', that is cold hardy, disease resistant, productive and bears an attractively colored fruit of good size and quality that is suitable for long distance shipping.

2 Drawing Sheets

FIELD OF THE INVENTION

The present invention relates to a peach variety and more specifically to a peach variety that is cold hardy, disease resistant, productive and bears attractively colored fruit of desirable size and quality.

BACKGROUND OF THE INVENTION

'AC Harrow Fair' is a fresh market peach which is distinguished in characteristics from the varieties similar to it, 'Harbrite', 'Harson' and 'Redhaven'. 'Harson' is the variety it most closely resembles. 'AC Harrow Fair' has been described by Richard E. C. Layne, HortScience, vol. 31(6): 1048–1049, October, 1996.

'AC Harrow Fair' Peach (*Prunus persica* (L.) Batsch) was released for the Ontario fresh market in 1996 following application for Plant Breeders Rights in Canada on Oct. 11, 1995 (Application No. 95-646). This variety was recommended for commercial introduction in Canada by members of the Western Ontario Fruit Testing Association (WOFTA) on the basis of generally favorable performance in regional trials in southern Ontario conducted by WOFTA. 'AC Harrow Fair' likely is adapted to northern regions where 'Redhaven' is grown successfully. To Applicant's knowledge, none of the prior art varieties referred to herein are patented.

SUMMARY OF THE INVENTION

The fruit of 'AC Harrow Fair' matures mid-season to late, slightly later than the reference varieties, and has stronger anthocyanin on the skin. The fruit are oblong in shape while the reference varieties have rounded fruit. 'AC Harrow Fair' has more than two nectaries on the petiole while the reference varieties have two. 'AC Harrow Fair' flowers later and for a longer duration than the reference varieties.

DETAILED DESCRIPTION OF THE INVENTION

Figure 1:
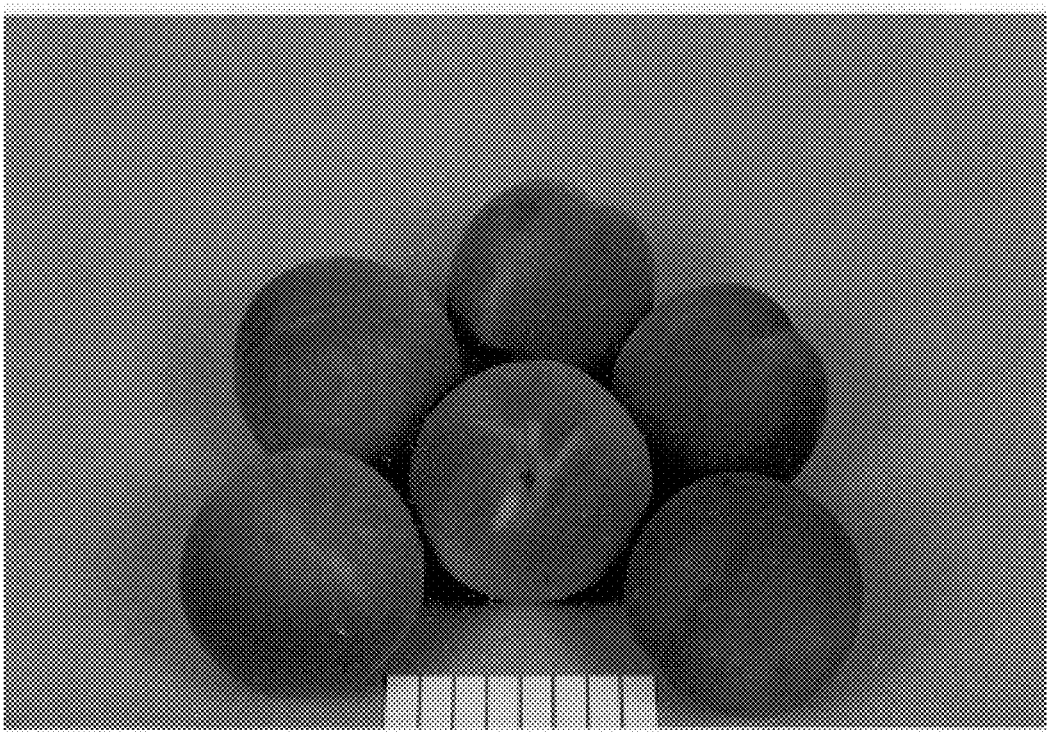
FIG. 1 is a photographic illustration of the whole fruit of 'AC Harrow Fair' Peach.
Figure 2:
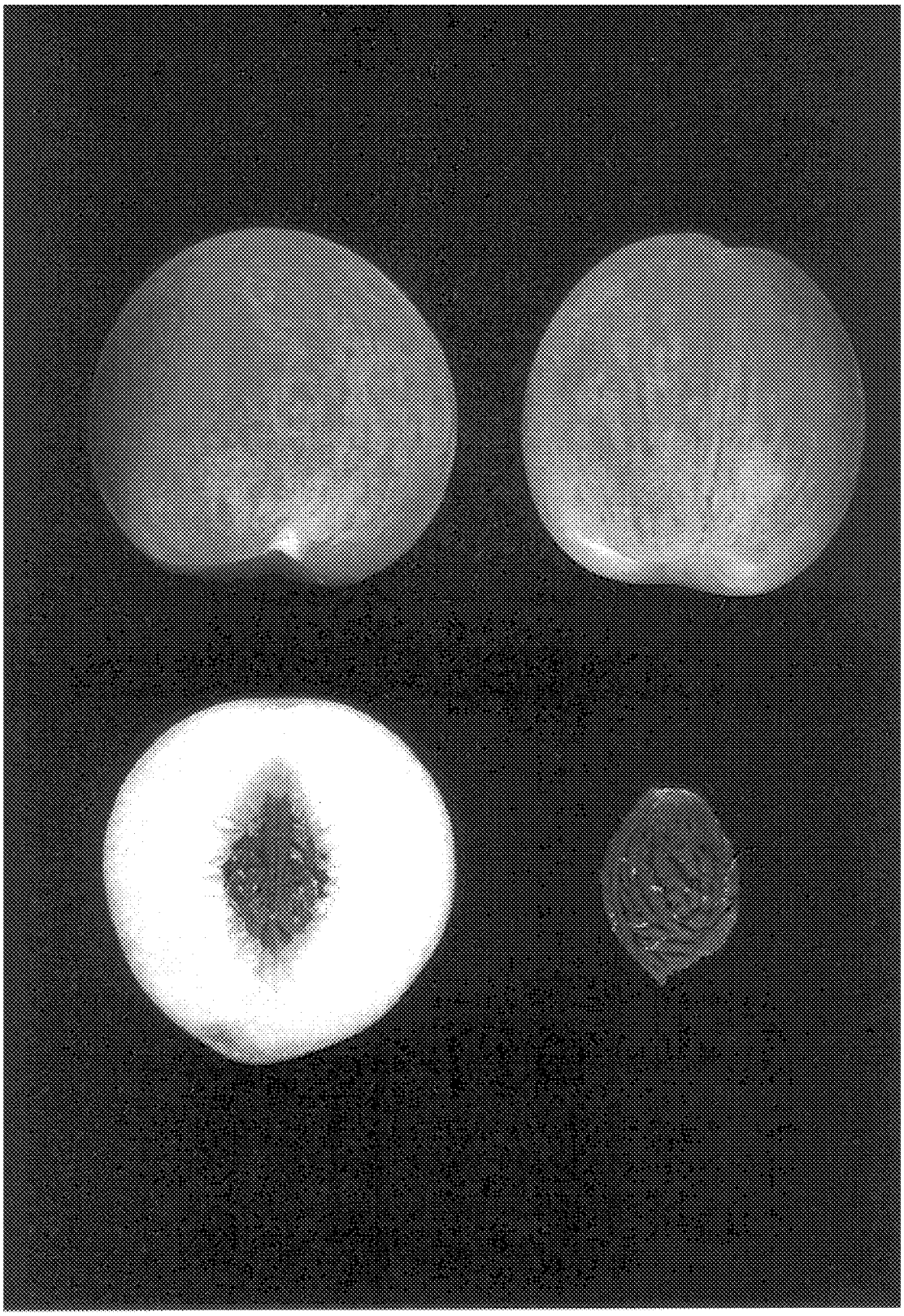
FIG. 2 is a photographic illustration of the whole fruit, bisected fruit and the stone. The color of the flesh, stone and stone cavity are illustrated.

'AC Harrow Fair' resulted from a controlled cross of 'Biscoe'×V55061, made at the Agriculture and Agri-Food Canada research station in Harrow, Ontario. 'Biscoe' originated from the cross 'Redskin'×'Raritan Rose' and V55061 originated from the cross 'Redskin'×'Kalhaven'. 'AC Harrow Fair' was selected as a seedling hybrid. It was then asexually propagated by budding on peach seedling rootstocks in Harrow, Ontario. It was tested under the experimental designation HW259 in regional trials coordinated by WOFTA. 'AC Harrow Fair' peach is uniform and stable through succeeding asexual propagation and the tree of this variety is self-pollinated. The color terminology is in accordance with The Royal Horticultural Society Colour Charts.

'AC Harrow Fair' is a non-spur type variety with strong vigor. The tree habit is semi-erect and the tree bark is reddish-brown in color in mid-summer and reddish-brown with a silvery sheen in winter. The leaves are medium in size for 'AC Harrow Fair' compared with the large size of 'Redhaven'. The leaf blade is up-folded in profile and the tip is recurved downwards. The angle at the base and tip of the leaf blade is acute. The leaf blade has no anthocyanin and the margins are serrated. The leaf petiole is medium in length for 'AC Harrow Fair' while 'Harson' is medium to long and 'Harbrite' is short to medium. The petiole has nectaries which are kidney-shaped for 'AC Harrow Fair' while they are round in shape for 'Harbrite'. 'AC Harrow Fair' normally has more than two nectaries while the reference varieties have two. There are no leaf stipules present.

The flowering shoot of 'AC Harrow Fair' has medium anthocyanin coloration. The density of flower buds is high for 'AC Harrow Fair' while the density is medium to high for 'Harson'. The flower buds are in groups of two or more. The time of beginning of flowering is late for 'AC Harrow Fair' while it is medium to late for 'Redhaven' and 'Harbrite'. Flower shape is campanulate and the calyx is reddish-brown in color. The petals are elongated in shape and small in size for 'AC Harrow Fair' while 'Harson' has medium sized petals and 'Harbrite' has small to medium sized petals. The petals are dark pink in color for 'AC Harrow Fair', medium pink for 'Harson' and violet pink for 'Harbrite'. Petal striping is absent and there are five petals per flower. The stamens of 'AC Harrow Fair' are equal in length when compared to the petals while they are longer for 'Redhaven'. There is one pistil and the stigma is positioned at the same level as the anthers. The anthers have pollen present and the ovary is pubescent. The duration of flowering is long for 'AC Harrow Fair', medium for 'Harson' and 'Harbrite' and medium to long for 'Redhaven'.

The fruit matures mid-season to late for 'AC Harrow Fair' while the reference varieties mature slightly earlier. The picking season is short for 'AC Harrow Fair' and long for 'Redhaven'. The tendency to natural falling of fruit is weak for 'AC Harrow Fair' and absent to very weak for 'Harson' and 'Redhaven'. Fruit size is large for 'AC Harrow Fair' and the shape of the fruit in profile view is oblong compared with the rounded shape of the reference varieties. The shape of the fruit tip is dimpled for 'AC Harrow Fair' while 'Redhaven' has a tipped shape. Symmetry along the suture is asymmetric for 'AC Harrow Fair' while the reference varieties are symmetric. The prominence of the suture is low for 'AC Harrow Fair' while it is medium for 'Redhaven'. The depth of the stem cavity is medium for 'AC Harrow Fair', medium to deep for 'Harson' and deep for 'Redhaven' and 'Harbrite'. The width of the stem cavity is medium for 'AC Harrow Fair' compared with the narrow width of the reference varieties. The ground color of the skin is yellow and anthocyanin coloration of the skin is bright red. The proportion of fruit skin with anthocyanin coloration is heavy to very heavy for 'AC Harrow Fair', heavy for 'Harson' and medium to heavy for 'Redhaven' and 'Harbrite'. The anthocyanin is marbled for 'AC Harrow Fair' and striated for 'Redhaven' and 'Harbrite'. 'AC Harrow Fair' has sparse pubescence on the skin while 'Redhaven' has medium pubescence. The skin is medium in thickness and adherence of the skin to the flesh is strong for 'AC Harrow Fair' while it is medium for 'Redhaven' and weak for 'Harbrite'. The fruit flesh is firm and the ground color of the flesh is yellow to orange-yellow. The fruit flesh is not stringy, has a melting texture and intermediate acidity. The flesh of 'AC Harrow Fair' is juicy. 'AC Harrow Fair' will hold for 2 to 3 weeks in common cold storage when picked shortly before ripening.

The stone of 'AC Harrow Fair' is elongate in shape and small to medium in size while 'Harson' and 'Redhaven' have slightly larger stones. The percentage of split or shattered stones is absent or very low for 'AC Harrow Fair' and slightly higher for the reference varieties. 'AC Harrow Fair' has slight adherence of the stone to the flesh. The stone of 'AC Harrow Fair' has a length of 34.9 mm, a width of 25.5 mm and a thickness of 17.1 mm.

'AC Harrow Fair' differs from 'Harson', the variety it most closely resembles for the following characteristics: leaf blade length and width, and petiole length are less for the former than the latter. 'AC Harrow Fair' has normally more than two petiolar glands whereas 'Harson' has usually two and sometimes only one. The density of flower buds is usually greater for 'AC Harrow Fair' than for 'Harson'. 'AC Harrow Fair' begins flowering later than 'Harson' and the flowering period is longer. It also has smaller petals that are darker pink than for 'Harson'. 'AC Harrow Fair' fruit ripen 11 days later than 'Harson' and are subject to more natural fruit drop than 'Harson'. Fruit shape of 'AC Harrow Fair' in profile view is oblong while that of Harson is rounded. 'AC Harrow Fair' fruit is asymmetric along the suture while 'Harson' is symmetric. The petiole cavity is shallower and broader with 'AC Harrow Fair' than for 'Harson'. There is more anthocyanin coloration on the skin for 'AC Harrow Fair' than for 'Harson' but not anthocyanin coloration of the flesh directly under the skin for the former but present for the latter. Anthocyanin coloration around the stone is absent for 'AC Harrow Fair' but present for 'Harson'. The stone of 'AC Harrow Fair' is smaller than for 'Harson' and there is a lower percentage of shattered stones. 'AC Harrow Fair' is slightly more subject to canker than 'Harson' but similar in hardiness.

Additional characteristics of 'AC Harrow Fair' peach and the reference varieties are shown in Chart 1 below.

CHART 1

Plant vigor: Average growth (length) of 1 year old shoots.
- *Harrow fair.*—471 mm.
- *Redhaven.*—443 mm.
- *Harson.*—376 mm.
- *Harbrite.*—439 mm.

Trunk size/texture: Average trunk size (circumference) of 4 year old trees:
- *Harrow fair.*—197 mm.
- *Redhaven.*—182 mm.
- *Harson.*—205 mm.
- *Harbrite.*—186 mm.

The trunks of all the trees are painted with white latex paint to protect them from sun damage and therefore is very difficult to determine colour and texture of the bark on the trunk.

Crotch angles: Branch size and crotch angles are controlled by training and pruning methods of the trees. The natural growth habit of the tree is therefore not seen since poorly angled (narrow) branches are pruned out. Remaining branches are approximately 70 degrees from vertical position of the central leader of the tree.

Color:
- *Fruit skin* (*ground color*).—Light yellow, 7A.
- *Fruit skin* (*blush*).—46A.
- *Flesh.*—16A.
- *Pit cavity.*—Yellow-orange 22A.
- *Pit.*—174A.
- *Leaf* (*dorsal*).—137A.
- *Leaf* (*ventral*).—138A.

Lenticels: Relative number and size:
- *Harrow Fair.*—few and very small (smaller than 1 mm).
- *Redhaven.*—very few and very small.
- *Harson.*—moderate number and very small.
- *Harbrite.*—few and very small.

Avg. bloom date/duration:
- *Harrow Fair.*—May 5, 4 days duration.

*Redhaven.*—May 5, 6 days.
*Harson.*—May 5, 4 days.
*Harbrite.*—May 4, 4 days.

Avg. ripe dates/duration:
*Harrow Fair.*—August 20, 4 days.
*Redhaven.*—August 13, 7 days.
*Harson.*—August 10, 4 days.
*Harbrite.*—August 15, 4 days.

Fruit characteristics:
*Harrow Fair.*—Height (mm)=68.0, Width (mm)=68.6, Weight (g)=176.8.
*Redhaven.*—Height (mm)=70.4, Width (mm)=73.9, Weight (g)=219.8.
*Harson.*—Height (mm)=68.6, Width (mm)=69.8, Weight (g)=186.8.
*Harbrite.*—Height (mm)=66.8, Width (mm)=70.1, Weight (g)=185.8.

Sugar content (brix):
*Harrow Fair.*—9.7.
*Redhaven.*—9.7.
*Harson.*—9.0.
*Harbrite.*—9.9.

Productivity: This is evaluated on a rating system from 1 to 10 where 1 is very little or no crop, 5 is a commercially acceptable amount of fruit on a tree, and 10 represents a crop load so heavy it would break the tree if left un-thinned. All the varieties mentioned for the descriptor having average ratings of 5.

Nectaries:
*Harrow Fair.*—kidney-shaped.
*Redhaven.*—kidney-shaped.
*Harson.*—kidney-shaped.
*Harbrite.*—round.

Petioles:
*Harrow Fair.*—Length (mm)=8.9, width (mm)=1.3.
*Redhaven.*—Length (mm)=9.9, width (mm)=1.4.
*Harson.*—Length (mm)=10.9, width (mm)=1.2.
*Harbrite.*—Length (mm)=8.8, width (mm)=1.2.

PERFORMANCE

The performance of 'AC Harrow Fair', in comparison with 'Harbrite', 'Harson' and 'Redhaven' is summarized in Table 1. Tests and trials were conducted at the Agriculture and Agri-Food Canada Research Station in Harrow, Ontario from 1990 to 1995. The trial consisted of three replications, in a completely randomized design, with trees spaced 3 meters apart within the row and 5.5 meters between rows.

TABLE 1

Comparison table for 'AC Harrow Fair'

| CHARACTERISTICS | 'AC HARROW FAIR' | 'HARSON'* |
|---|---|---|
| Length of leaf blade (mm) | | |
| mean | 136.0 | 153.1 |
| range | 111–165 | 129–174 |
| standard deviation | 12.4 | 11.5 |
| number measured | 30 | 30 |
| Width of leaf blade (mm) | | |
| mean | 32.7 | 35.9 |
| range | 27–38 | 31–41 |
| standard deviation | 3.0 | 3.1 |
| number measured | 30 | 30 |
| Duration of flowering | long | medium |
| Petal color | dark pink | medium pink |
| Shape of fruit | oblong | rounded |
| Proportion of fruit surface with anthocyanin coloration on the skin | heavy to very heavy (±75%) | heavy (±75%) |
| Adherence of fruit skin to flesh | strong | strong |
| **CHARACTERISTICS** | **'REDHAVEN'*** | **'HARBRITE'*** |
| Length of leaf blade (mm) | | |
| mean | 151.4 | 134.5 |
| range | 131–172 | 104–152 |
| standard deviation | 9.9 | 12.3 |
| number measured | 30 | 30 |
| Width of leaf blade (mm) | | |
| mean | 35.9 | 33.3 |
| range | 32–40 | 27–39 |
| standard deviation | 2.3 | 3.4 |
| number measured | 30 | 30 |
| Duration of flowering | medium to long | medium |
| Petal color | dark pink | violet pink |
| Shape of fruit | rounded | rounded |
| Proportion of fruit surface with anthocyanin coloration on the skin | medium to heavy (50–75%) | medium to heavy (50–75%) |
| Adherence of fruit skin to flesh | medium | weak |

*reference varieties

I claim:

1. A new and distinct peach tree variety substantially as shown and described herein.

* * * * *